US010881302B2

(12) United States Patent
Tal et al.

(10) Patent No.: US 10,881,302 B2
(45) Date of Patent: Jan. 5, 2021

(54) SYSTEM, METHOD AND COMPUTER READABLE MEDIUM FOR DETERMINING A CORE TEMPERATURE OF A PERSON

(71) Applicant: Lifewatch Technologies Ltd., Rehovot (IL)

(72) Inventors: Benny Tal, Ashkelon (IL); Gal Goshen, Neve Oranim (IL); Yossi Lovton, Nes Ziona (IL)

(73) Assignee: LIFE WATCH TECHNOLOGIES LTD., Rehovot (IL)

(*) Notice: Subject to any disclaimer, the term of this patent is extended or adjusted under 35 U.S.C. 154(b) by 106 days.

(21) Appl. No.: 14/911,242

(22) PCT Filed: Aug. 20, 2014

(86) PCT No.: PCT/IL2014/050748
§ 371 (c)(1),
(2) Date: Feb. 9, 2016

(87) PCT Pub. No.: WO2015/029014
PCT Pub. Date: Mar. 5, 2015

(65) Prior Publication Data
US 2016/0174851 A1 Jun. 23, 2016

Related U.S. Application Data

(63) Continuation of application No. 13/975,431, filed on Aug. 26, 2013, now abandoned.

(51) Int. Cl.
*A61B 5/01* (2006.01)
*A61B 5/00* (2006.01)

(52) U.S. Cl.
CPC . *A61B 5/01* (2013.01); *A61B 5/72* (2013.01)

(58) Field of Classification Search
CPC ........ A61B 5/01; A61B 5/015; G01K 13/002; G01K 13/004; G01K 7/02; G01K 7/003; G01K 15/00; G01K 7/12
USPC ........................................................ 600/549
See application file for complete search history.

(56) References Cited

U.S. PATENT DOCUMENTS

| 8,275,413 B1* | 9/2012 | Fraden ............... H04M 1/72522 455/344 |
| 8,452,382 B1 | 5/2013 | Roth |
| 2005/0064902 A1 | 3/2005 | Goris et al. |
| 2008/0246625 A1* | 10/2008 | Chen .................... G01J 5/0022 340/686.6 |
| 2009/0325639 A1 | 12/2009 | Koehn |

(Continued)

OTHER PUBLICATIONS

European Office Action dated Mar. 22, 2017.*
(Continued)

*Primary Examiner* — David J. McCrosky
(74) *Attorney, Agent, or Firm* — Chang B. Hong

(57) ABSTRACT

A computerized method for detecting a core temperature of a person, the method may include: receiving multiple temperature readings obtained by scanning a temperature sensor across a skin area of a person, the skin area covers at least one blood vessel, to provide multiple temperature readings; the multiple temperature readings include a peak temperature reading; and determining, by a processor, an estimate of the core temperature of the person in response to at least one temperature reading that differs from the peak temperature reading.

20 Claims, 10 Drawing Sheets

(56) References Cited

U.S. PATENT DOCUMENTS

| | | | |
|---|---|---|---|
| 2012/0029308 A1 | 2/2012 | Paquet | |
| 2012/0220835 A1 | 8/2012 | Chung | |
| 2014/0046192 A1* | 2/2014 | Mullin | H05K 13/00 |
| | | | 600/474 |
| 2016/0157732 A1* | 6/2016 | Tanaka | A61B 5/01 |
| | | | 600/474 |
| 2016/0213325 A1* | 7/2016 | Sogo | A61B 5/015 |

OTHER PUBLICATIONS

Internet Archive, Global Sources Forehead Thermometer, Jul. 3, 2013. Retrieved from <https://web.archive.org/web/20130703124313/http://www.globalsources.com/manufacturers/Forehead-Thermometer.html> on Apr. 20, 2018.*

Google Search Results for "infrared thermometer (iphone or android or smartphone)" limited to dates before Aug. 26, 2013.*

* cited by examiner

US 10,881,302 B2

SYSTEM, METHOD AND COMPUTER READABLE MEDIUM FOR DETERMINING A CORE TEMPERATURE OF A PERSON

BACKGROUND OF THE INVENTION

The core temperature of a person can provide an indication about the health of the person. The core temperature can be estimated by dedicated devices such as mercury based thermometers and infrared measurement devices that estimate the heat radiation that is radiated from a skin of the person.

It has been found that the detecting of the core temperature based upon peak temperatures is highly inaccurate as the measurement process is subjected to noises.

There is a growing need to provide efficient and accurate systems, methods and computer readable medium for providing accurate temperature measurements.

SUMMARY OF THE INVENTION

According to an embodiment of the invention there may be provided a computerized method for detecting a core temperature of a person, the method may include: receiving multiple temperature readings obtained by scanning a temperature sensor across a skin area of a person, the skin area covers at least one blood vessel, to provide multiple temperature readings; the multiple temperature readings comprise a peak temperature reading; and determining, by a processor, an estimate of the core temperature of the person in response to at least one temperature reading that differs from the peak temperature reading.

The determining may be made regardless of the peak temperature reading.

The determining may be responsive to a percentile of the temperature readings that ranges between 70 and 90 percent.

The determining may be responsive to a percentile of the temperature readings that ranges between 80 and 90 percent.

The determining may be responsive to an eighty seven percentile of the temperature readings.

The determining may include: calculating an intermediate estimate of the core temperature in response to the at least one temperature reading that differs from the peak temperature reading; and updating the intermediate estimate to provide the estimate of the core temperature of the person by applying a correction function that at least partially compensates for inaccuracies associated with the temperature readings.

The applying of the correction function may include applying a correction factor that ranges between 2 degrees to half a degree and wherein a value of the correction factor increases with an increase of the value of the intermediate estimate.

The applying of the correction function may include applying a correction factor on intermediate estimate values that are below a temperature threshold and preventing from applying the correction actor for intermediate estimate values that are above the temperature threshold.

The determining may be responsive to an age of the person.

The method may include increasing a value of the estimate of the core temperature of the person with an increase of age of the person.

The method may include increasing a value of the estimate of the core temperature of the person in a non-linear manner with an increase of age of the person.

The method may include decreasing a value of the estimate of the core temperature of the person with a decrease of age of the person.

The determining may be responsive to a gender of the person.

The determining may be responsive to a color attribute of the skin area.

The method further may include obtaining the multiple temperature readings by scanning the temperature sensor across the skin area of the person.

The temperature sensor may be embedded in a mobile phone.

The temperature sensor may be embedded within a sidewall of a mobile phone.

The temperature sensor may be embedded within a back panel of a mobile phone.

The temperature sensor may be included in a mobile phone; wherein the temperature readings are obtained without direct contact between the temperature sensor and the skin area.

The temperature sensor may be partially isolated from heat generated by the processor.

The processor may be at least partially surrounded by a heat dissipating shield.

According to an embodiment of the invention there may be provided a device that may include: a temperature sensor that may be arranged to generate multiple temperature readings obtained when scanning a skin area of a person, the skin area covers at least one blood vessel, the multiple temperature readings comprise a peak temperature reading; and a processor that may be arranged to determine an estimate of the core temperature of the person in response to at least one temperature reading that differs from the peak temperature reading.

According to an embodiment of the invention there may be provided a non-transitory computer readable medium that stores instructions for: receiving multiple temperature readings obtained by scanning a temperature sensor across a skin area of a person, the skin area covers at least one blood vessel, to provide multiple temperature readings; the multiple temperature readings comprise a peak temperature reading; and determining, by a processor, an estimate of the core temperature of the person in response to at least one temperature reading that differs from the peak temperature reading.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof may best be understood by reference to the following detailed description when read with the accompanying drawings in which:

Figure 1A:
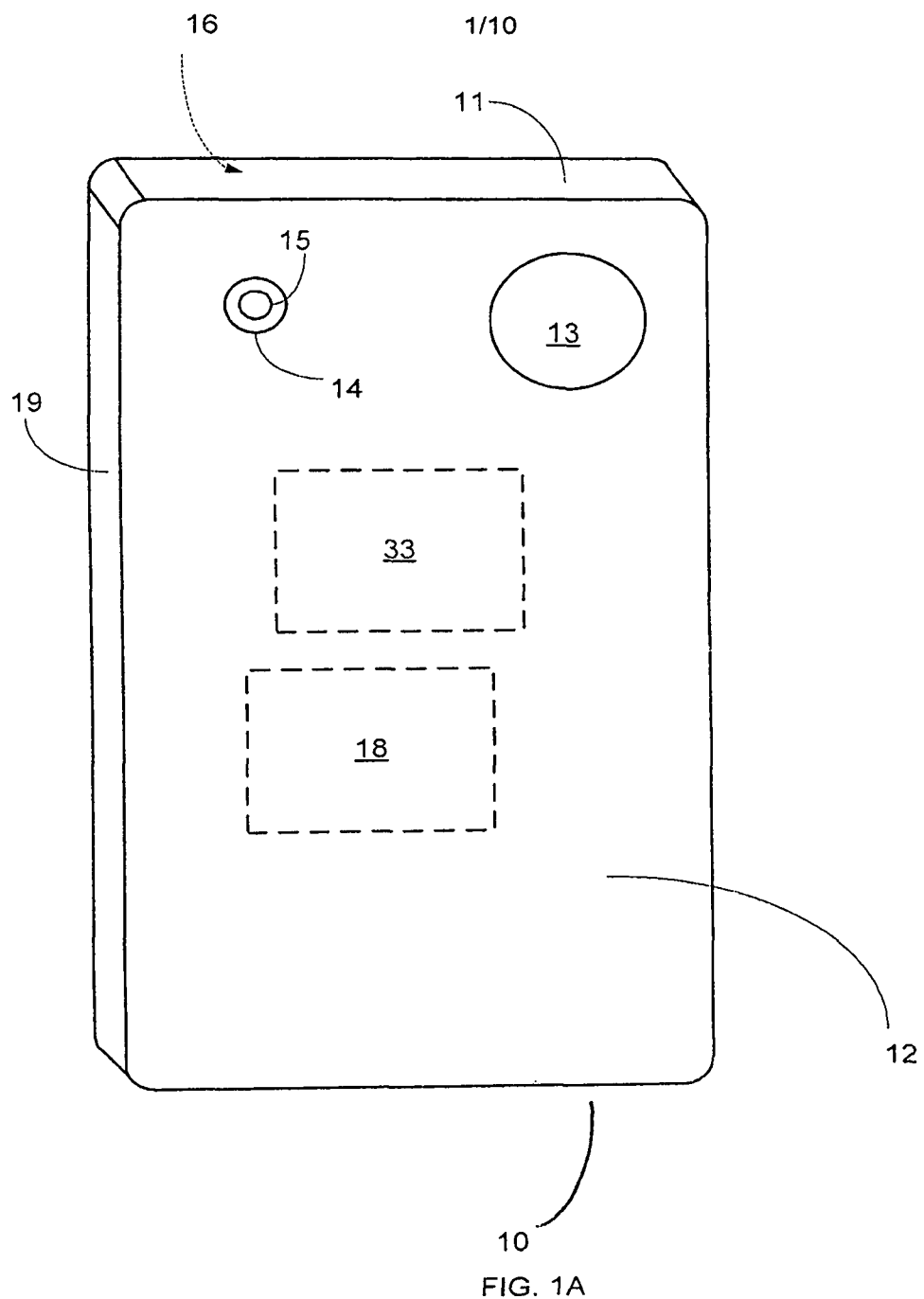
FIG. 1A illustrates a mobile phone according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE DRAWINGS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

The term "core temperature" means the temperature of deep structures of the body, such as the liver, that differs from the temperature of the skin.

FIG. 1A illustrates a mobile phone 10 according to an embodiment of the invention. The mobile phone 10 may have a touch screen 16, a back panel 12 and sidewalls such as upper sidewall 11 and left sidewall 19. FIG. 1A that back panel 12 as including an opening for a lens 13 of a camera and an opening 14 that reveals a temperature sensor 15 that is proximate to the back panel 12. Mobile phone 10 includes a processor such as processor 33.

Figure 1B:
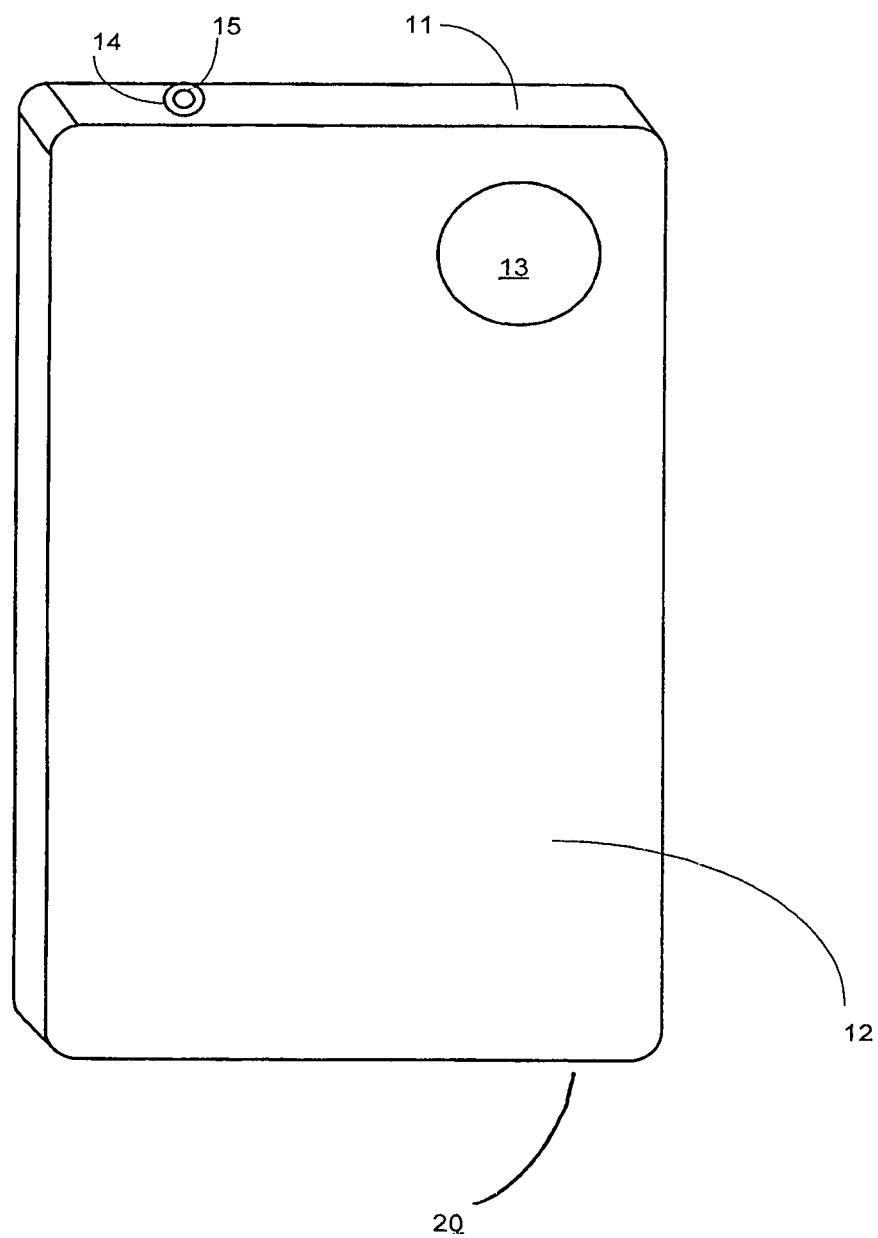
FIG. 1B illustrates a mobile phone according to an embodiment of the invention.

FIG. 1B illustrates the mobile phone 20 as including the opening 14 at its upper sidewall 14 and this opening reveals the temperature sensor 15 that is proximate to its upper sidewall 11.

A person may scan a skin area in various manners—he may scan the skin area without contacting the skin area by the mobile phone or while contacting the skin area.

Because the temperature readings may be affected by the distance between the skin area and temperature sensor it may be desirable to maintain a contact distance between the skin area and the temperature sensor. Thus, contacting the skin area during the scan can provide better results.

Furthermore—placing the temperature sensor in proximity to the area of the mobile phone that contacts the person may provide better results—as it is easier to maintain the same distance to the skin. Contacting the skin by a region of the mobile phone that is less proximate to the temperature sensor may provide less accurate temperature readings. This inaccuracy can be tolerated but may be compensated by measuring, during the scan the spatial relationship between the temperature sensor and the skin, and compensating for distance changes accordingly. The changes in spatial relationship can be estimated by accelerometer/gyroscopes, orientation sensors of the mobile phone (auxiliary sensors 18 of FIG. 1A), by dedicated optical and other distance measurement devices and the like. The relationship between distance (between the temperature sensor and the skin) can be measured or fed to the mobile phone. This relationship can be calculated given the ambient temperature or regardless of the ambient temperature.

Figure 3A:
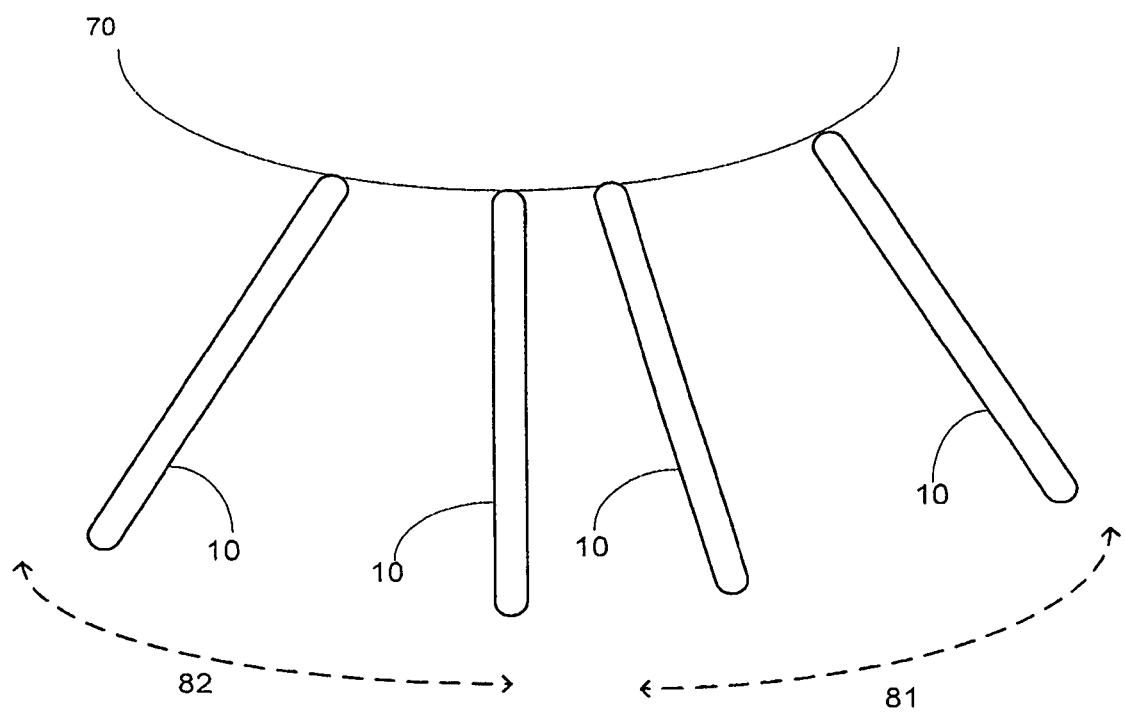
FIG. 3A illustrates a scanning process according to an embodiment of the invention.
Figure 3B:
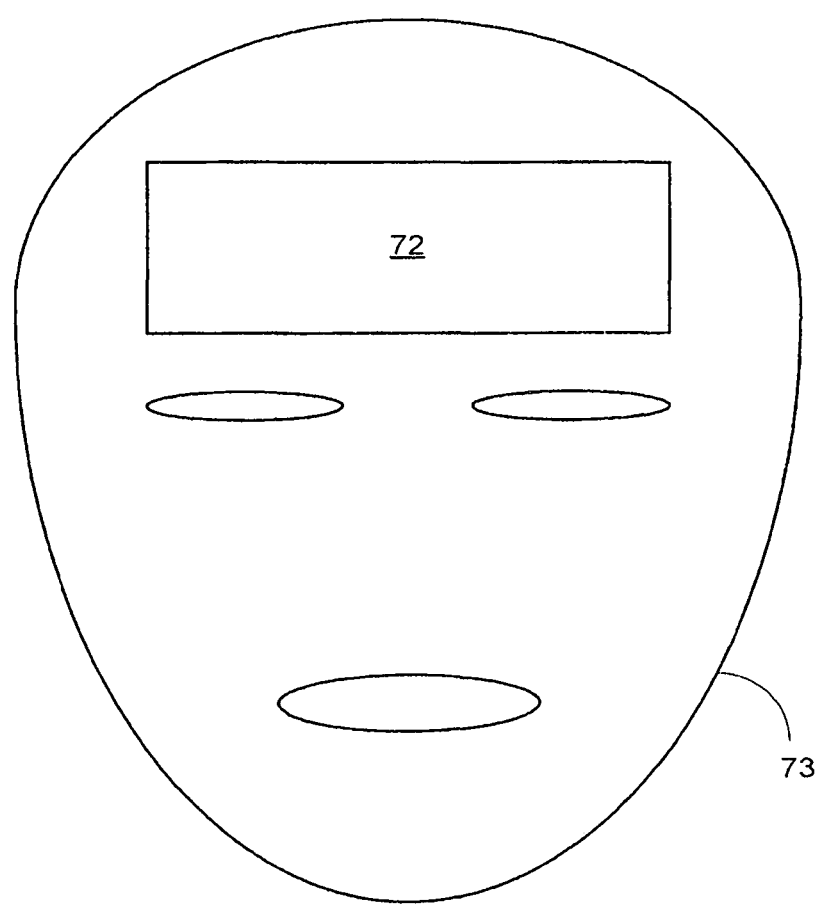
FIG. 3B illustrates a scanned area according to an embodiment of the invention.

FIGS. 3A and 3B illustrate a scanning of a skin area 72 of a forehead 70 of a person 73 while contacting the skin area by the upper sidewall 11 of the mobile phone 10. Arrows 81 and 82 of FIG. 3A illustrate the scanning process. It is noted that other skin areas can be scanned.

It should be noted that using a mobile phone such as mobile phone 20 may provide more accurate temperature readings than those obtained by mobile phone 10—as mobile phone 20 includes the temperature sensor 15 at the upper sidewall 11 that contacts the skin of the person. These differences can be tolerated or at least partially compensated by measuring the spatial relationship between the temperature sensor and the skin as a function of the orientation of the mobile phone and/or distance between the mobile phone and skin.

Figure 2:
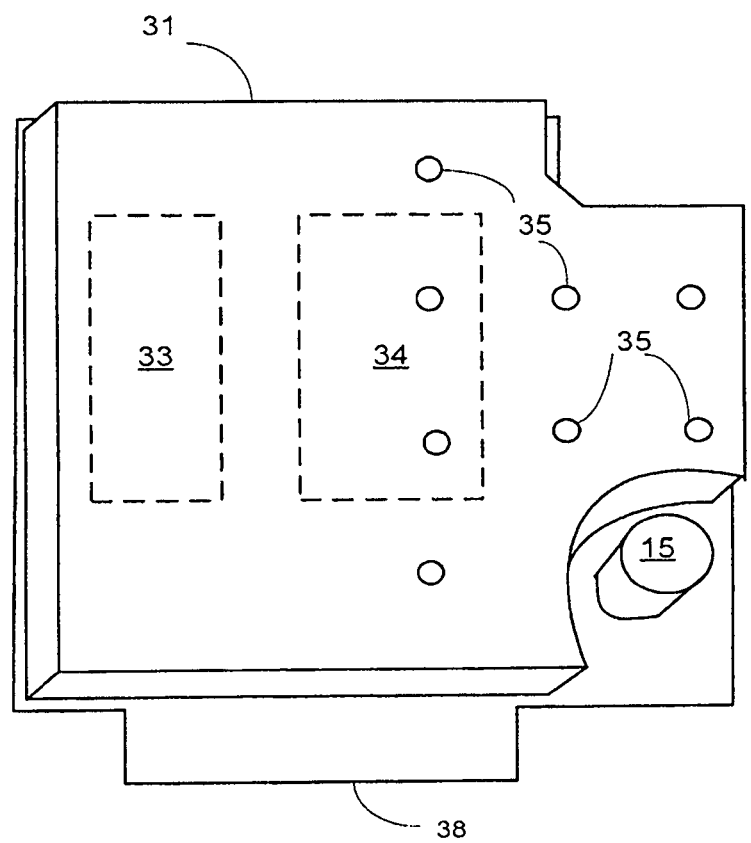
FIG. 2 illustrates a temperature sensor and its surroundings according to an embodiment of the invention.

FIG. 2 illustrates a temperature sensor 15 and its surroundings according to an embodiment of the invention.

Figure 4:
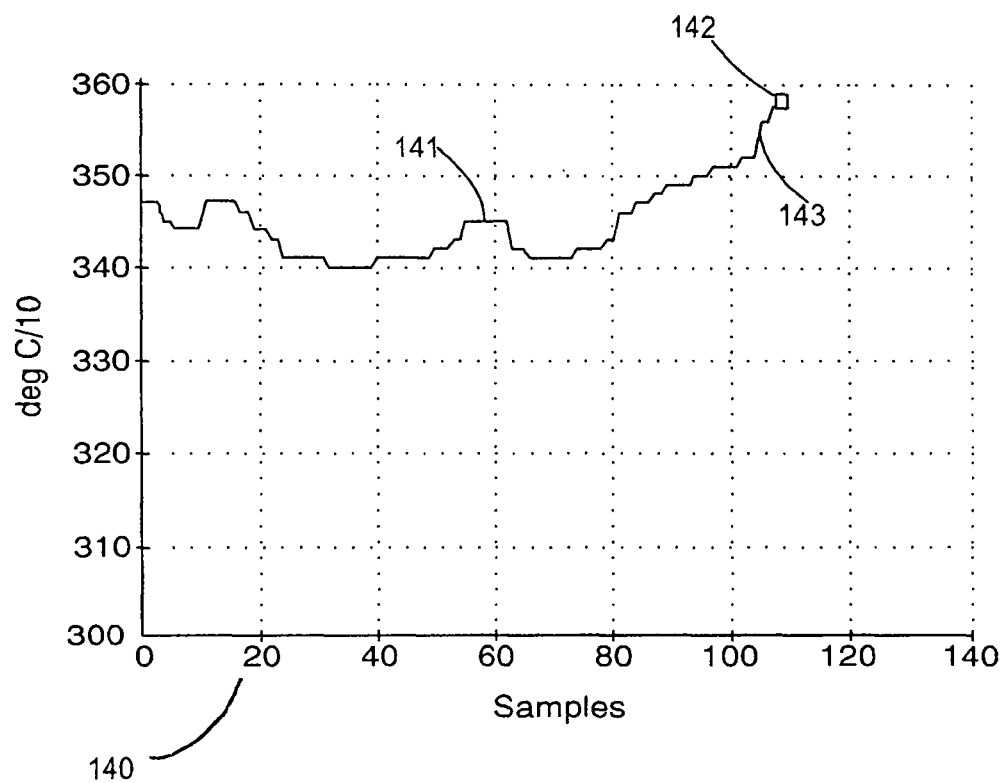
FIG. 4 illustrates temperature readings according to an embodiment of the invention.

The mobile phone includes multiple integrated circuits that may be used for short range communication, long range communication, processing tasks and the like. It has been found that the heat dissipated from various electrical components (including integrated circuits) of the mobile phone can affect the temperature readings of the temperature sensor 15. According to an embodiment of the invention the temperature sensor 15 is proximate to a shield 31 that assists in effectively dissipating the heat from such components (integrated circuits 33 and 34 of FIG. 2) in order to reduce thermal noise introduced by these components. FIG. 2 illustrates the shield 31 as including ventilation openings 35 and be connected to an integrated circuit 38 that is also connected to the temperature sensor 15. The shield may be required especially when due to size and/or weight constraints the temperature sensor cannot be surrounded by a relatively heavy and large heat sink FIG. 4 illustrates temperature readings (curve 141 of graph 140) according to an embodiment of the invention. The curve 141 represents multiple temperature readings obtained during a scanning of a skin area. Curve 141 includes a noisy peak temperature 142 that may be ignored off when determining the core temperature of the person. FIG. 4 illustrates an eighty seven percentile reading 143 that can be used for determining the core temperature.

The calculation of the core temperature can include selecting multiple temperature readings while ignoring the peak temperature reading and applying a statistical function on the selected temperature readings. By ignoring the peak temperature reading which is expected to exhibit a relatively high noise component, the measurement can be more accurate. Furthermore, the scanning process may provide fluctuating temperature readings, especially when the scanning does not maintain a fixed distance between the temperature sensor and the scanned skin and this fluctuation can be at least partially compensated by removing extreme temperature readings such as the peak temperature reading.

Figure 5:
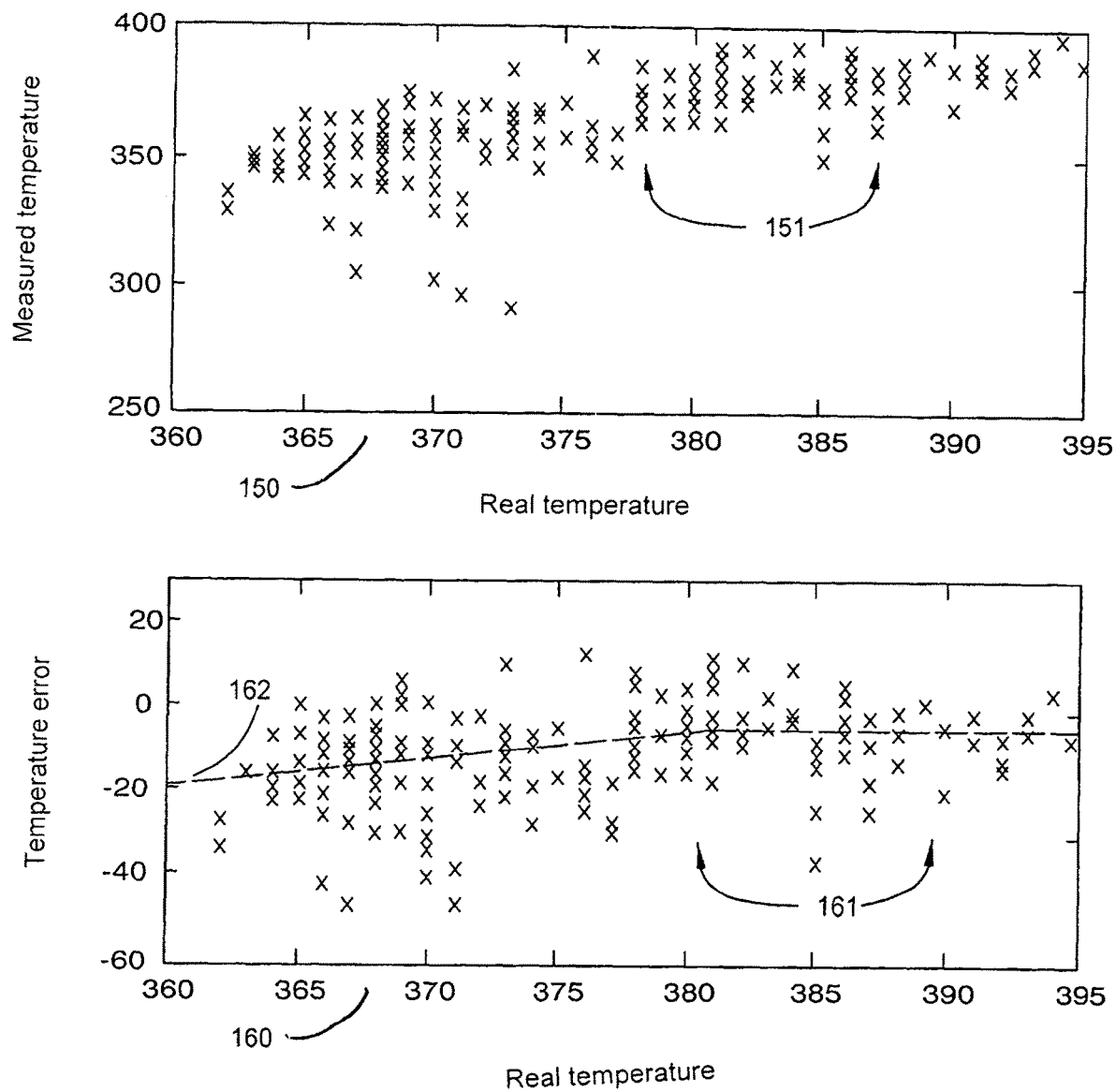
FIG. 5 illustrates multiple temperature readings and an error correction factor according to an embodiment of the invention.

FIG. 5 illustrates multiple temperature readings 151 and an error correction factor 162 according to an embodiment of the invention.

Graph 150 includes multiple points—each point ("x") represents a relationship between the real temperature and a temperature reading. The x-axis of graph 150 illustrates the real temperatures (multiplied by ten) while the y-axis of graph shows measured temperatures (multiplied by tem) as measured during a scan of a skin area by a mobile phone that includes a temperature sensor such as those illustrated in FIGS. 1A).

Graph 160 includes multiple points—each point ("x") represents a relationship between a temperature error (difference between real and measured temperatures as illustrated in graph 150) and the real temperature. The y-axis of graph 160 illustrates the temperature error (multiplied by ten) and the x-axis of graph 160 illustrates the real temperature.

Graph 160 also includes curve 162 that represents a correction function. The values of the correction function (correction factors) range between 2 degrees to half a degree and increases (in a non-linear function) with an increase of the value of the temperature reading (or real temperature).

Figure 6:
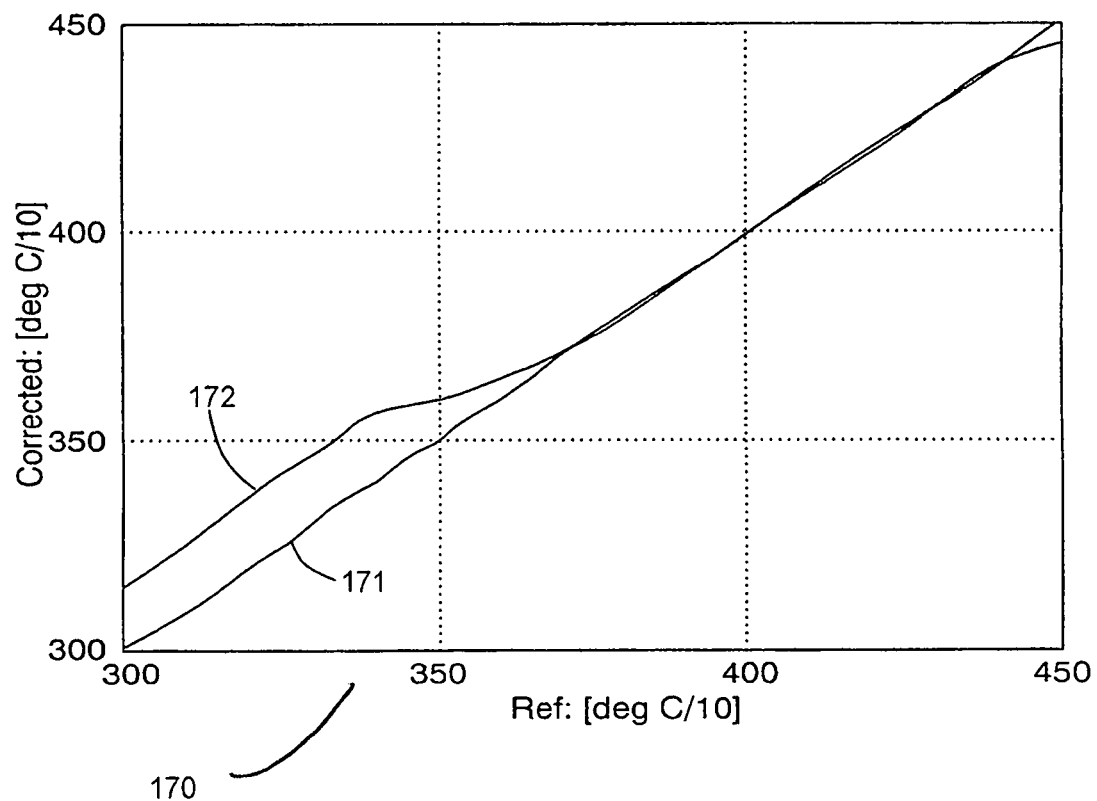
FIG. 6 illustrates an error correction factor according to an embodiment of the invention.

FIG. 6 illustrates an error correction factor 172 according to an embodiment of the invention. In order to lower the chance of the mobile phone showing an output which is significantly lower than 36 degrees, a correction of the temperature readings (171) is added. The correction factor is constant between 30 and 34 degrees and gradually decreases between 34 and 36 degrees. Other correction factors can be applied.

Figure 7:
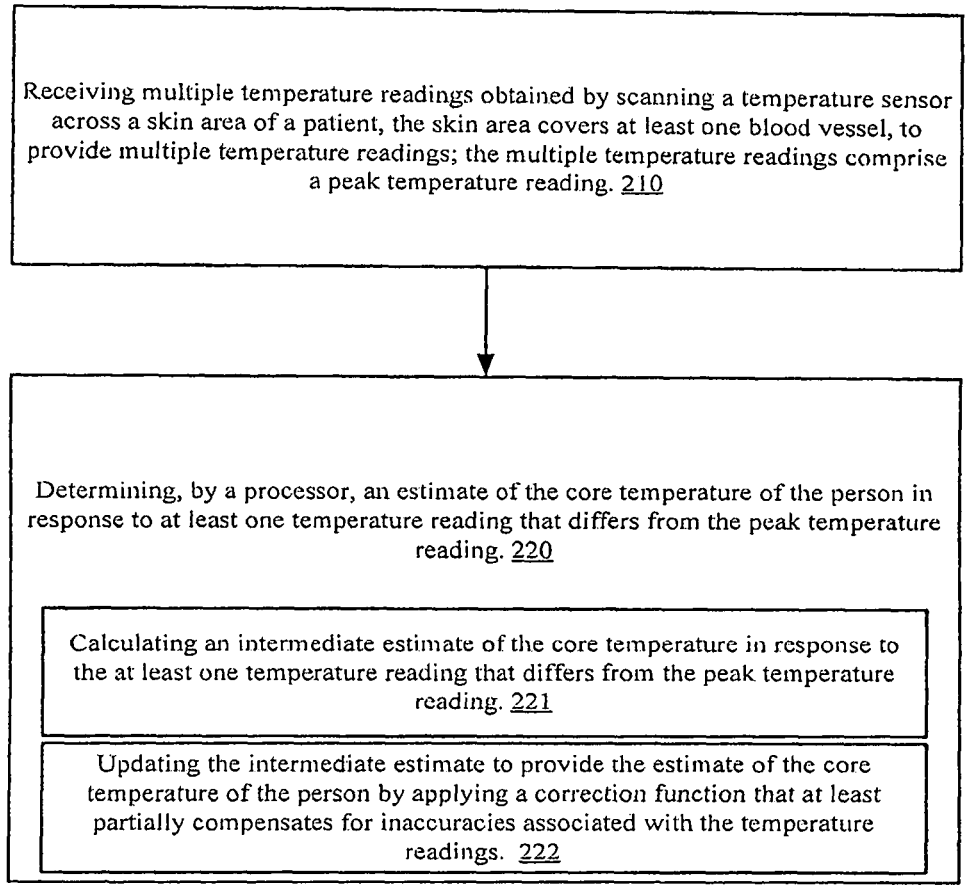
FIG. 7 illustrates a method according to an embodiment of the invention.

FIG. 7 illustrates method 200 according to an embodiment of the invention.

Method 200 may start by stage 210 of receiving multiple temperature readings obtained by scanning a temperature sensor across a skin area of a person, the skin area covers at least one blood vessel, to provide multiple temperature readings; the multiple temperature readings comprise a peak temperature reading.

Stage 210 may be followed by stage 220 of determining, by a processor, an estimate of the core temperature of the person in response to at least one temperature reading that differs from the peak temperature reading.

The determining may be made regardless of the peak temperature reading.

The determining may be responsive to a percentile of the temperature readings that ranges between 70 and 90 percent.

The determining may be responsive to a percentile of the temperature readings that ranges between 80 and 90 percent.

The determining may be responsive to an eighty seven percentile of the temperature readings.

The determining may include calculating (221) an intermediate estimate of the core temperature in response to the at least one temperature reading that differs from the peak temperature reading; and updating (222) the intermediate estimate to provide the estimate of the core temperature of the person by applying a correction function that at least partially compensates for inaccuracies associated with the temperature readings.

The applying of stage 222 may include applying a correction factor that ranges between 2 degrees to half a degree and wherein a value of the correction factor increases with an increase of the value of the intermediate estimate.

The applying of stage 222 may include applying a correction factor on intermediate estimate values that are below a temperature threshold and preventing from applying the correction actor for intermediate estimate values that are above the temperature threshold.

The determining (220) may be responsive to an age of the person. This may include increasing a value of the estimate of the core temperature of the person with an increase of age of the person, decreasing the value of the estimate of the core temperature of the person with an increase of age. The increment or decrement can include applying linear or non-linear corrections. The age may be fed by the person or by another party.

The determining (220) may be responsive to a gender of the person. This may include increasing a value of the estimate of the core temperature of the person with an increase of gender of the person, decreasing the value of the estimate of the core temperature of the person with an increase of gender. The increment or decrement can include applying linear or non-linear corrections. The gender may be fed by the person or by another party.

The determining (220) may be responsive to a skin attribute (color of skin, brightness of skin, and perspiration of skin) of the person. This may include increasing a value of the estimate of the core temperature of the person with an increase of skin attribute of the person, decreasing the value of the estimate of the core temperature of the person with an increase of skin attribute. The increment or decrement can include applying linear or non-linear corrections. The skin attribute may be fed by the person or by another party.

Figure 8:
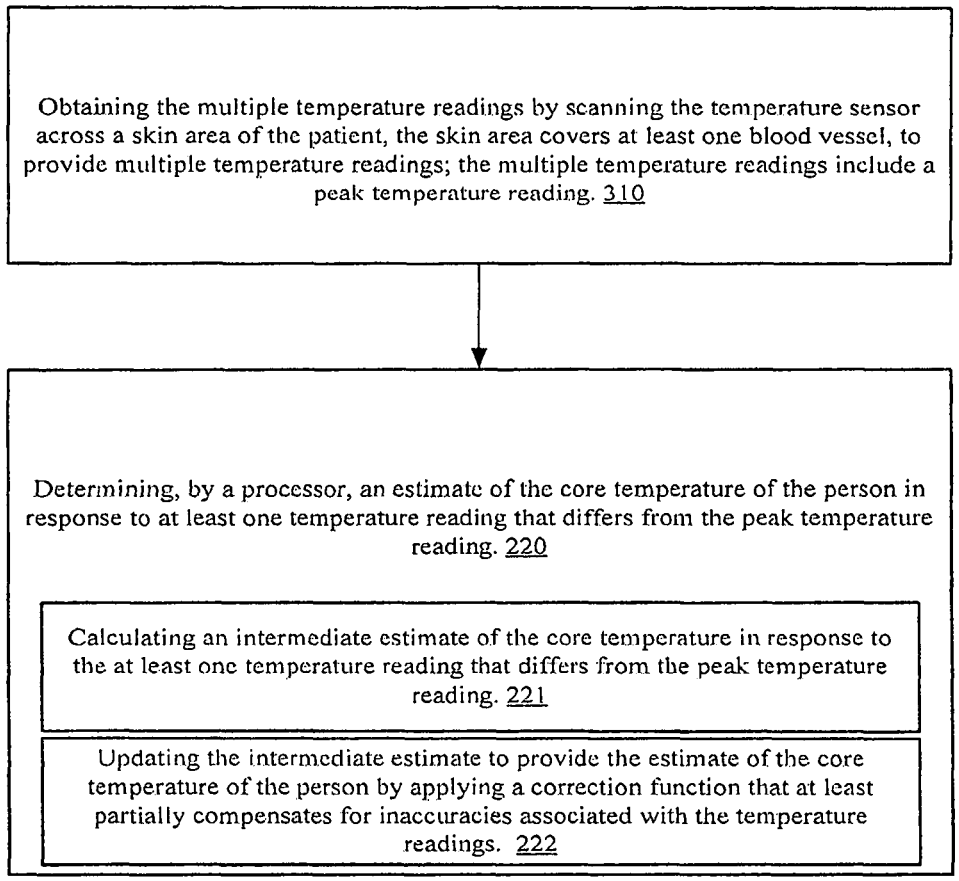
FIG. 8 illustrates a method according to an embodiment of the invention.

FIG. 8 illustrates method 300 according to an embodiment of the invention.

Method 300 may start by stage 310 of obtaining the multiple temperature readings by scanning the temperature sensor across a skin area of the person, the skin area covers at least one blood vessel, to provide multiple temperature readings; the multiple temperature readings include a peak temperature reading.

Stage 310 may be followed by stage 220 of determining, by a processor, an estimate of the core temperature of the person in response to at least one temperature reading that differs from the peak temperature reading.

The scanning of stage 310 may include scanning by a temperature sensor that may be embedded in a mobile phone, may be embedded within a sidewall of a mobile phone, may be embedded within a back panel of a mobile phone, may be performed with or without direct contact between the temperature sensor and the skin area, may be performed by a temperature sensor that is partially isolated from heat generated by the processor.

The invention may also be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a non-transitory computer readable medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein may be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A computerized method for detecting a core temperature of a person, the method comprising:
   receiving multiple temperature readings obtained by scanning a temperature sensor across a skin area of a person, the skin area covers at least one blood vessel, to provide multiple temperature readings, wherein the multiple temperature readings comprise a peak temperature reading,
   receiving upon scanning, from one or more auxiliary sensors, a spatial measurement associated with a distance between the skin area of the person and the temperature sensor,
   determining, by a processor, an estimate of the core temperature of the person in response to at least one temperature reading that differs from the peak temperature reading, and the distance between the skin area of the person and the temperature sensor, wherein the estimate is determined by calculating an intermediate estimate of the core temperature by selecting the received temperature readings that fall within a range between 70 and 90 percent of the peak temperature reading, and by dynamically compensating for the measured distance.
   taking an average of received temperature readings in that range as the intermediate range,
   updating the intermediate estimate by applying a correction function that at least partially compensates for inaccuracies associated with the temperature readings, wherein the correction function is determined by measuring errors in temperature readings, over a range of temperatures, occurring when scanning the temperature sensor across a skin area of a person, and
   applying the correction function to provide for a given measured temperature, a temperature to add to the intermediate estimate to determine the estimate of the core temperature of the person.

2. The method according to claim 1, wherein the determining is made regardless of the peak temperature reading.

3. The method according to claim 1, wherein the determining of the core temperature is based on a percentile of the temperature readings that ranges between 80 and 90 percent.

4. The method according to claim 1, wherein the determining of the core temperature is based on an eighty seven percentile of the temperature readings.

5. The method according to claim 1, wherein the applying of the correction function comprises applying a correction factor that ranges between 2 degrees to half a degree and wherein a value of the correction factor increases with an increase of the value of the intermediate estimate.

6. The method according to claim 1, wherein the determining of the core temperature is associated with an age of the person.

7. The method according to claim 1, comprising increasing a value of the estimate of the core temperature of the person with an increase of age of the person.

8. The method according to claim 1, comprising increasing a value of the estimate of the core temperature of the person in a non-linear manner with an increase of age of the person.

9. The method according to claim 1, comprising decreasing a value of the estimate of the core temperature of the person with a decrease of age of the person.

10. The method according to claim 1, wherein the determining of the core temperature is associated with a gender of the person.

11. The method according to claim 1, wherein the determining of the core temperature is associated with a color attribute of the skin area.

12. The method according to claim 1, wherein the received temperature readings were obtained from a temperature sensor is embedded in a mobile phone.

13. The method according to claim 12, wherein the temperature sensor is embedded within a sidewall of a mobile phone.

14. The method according to claim 12, wherein the temperature sensor is embedded within a back panel of a mobile phone.

15. The method according to claim 12, wherein the temperature sensor is included in a mobile phone; wherein the temperature readings are obtained without direct contact between the temperature sensor and the skin area.

16. The method according to claim 12, wherein the temperature sensor is partially isolated from heat generated by the processor.

17. The method according to claim 12, wherein the processor is at least partially surrounded by a heat dissipating shield.

18. The method of claim 1, wherein the one or more auxiliary sensors is selected from the group consisting of: an accelerometer, a gyroscope and an orientation sensor.

19. A non-transitory computer readable medium that stores instructions for:
receiving multiple temperature readings obtained by scanning a temperature sensor across a skin area of a person, the skin area covers at least one blood vessel, to provide multiple temperature readings, wherein the multiple temperature readings comprise a peak temperature reading,
receiving upon scanning, from one or more auxiliary sensors, a spatial measurement associated with a distance between the skin area of the person and the temperature sensor,
determining, by a processor, an estimate of the core temperature of the person in response to at least one temperature reading that differs from the peak temperature reading, and the distance between the skin area of the person and the temperature sensor, wherein the estimate is determined by calculating an intermediate estimate of the core temperature by selecting the temperature readings that fall within a range between 70 and 90 percent of the peak temperature reading, and by dynamically compensating for the measured distance,
taking an average temperature reading in that range as the intermediate estimate,
updating the intermediate estimate by adding a correction function that at least partially compensates for inaccuracies associated with the temperature readings, wherein the correction function is determined by measuring errors in temperature readings, over a range of temperatures, occurring when scanning the temperature sensor across a skin area of a person, and
applying the correction function to provide for a given measured temperature, a temperature to add to the intermediate estimate to determine the estimate of the core temperature of the person.

20. The non-transitory computer readable medium of claim 19, wherein the one or more auxiliary sensors is selected from the group consisting of: an accelerometer, a gyroscope and an orientation sensor.

* * * * *